(12) United States Patent
Essayem et al.

(10) Patent No.: US 9,090,580 B2
(45) Date of Patent: Jul. 28, 2015

(54) METHOD FOR PREPARING FURFURAL

(75) Inventors: Nadine Essayem, Saint Just Chaleyssin (FR); Rodrigo Lopez De Souza, Rio de Janerio (BR); Franck Rataboul, Lyons (FR); Aude-Claire Doiseau, Lyons (FR)

(73) Assignees: CENTRE NATIONAL DE LA RECHERCHE SCIENTIFIQUE (C.N.R.S.), Paris (FR); UNIVERSITE CLAUDE BERNARD LYON I, Villeurbanne (FR)

( * ) Notice: Subject to any disclaimer, the term of this patent is extended or adjusted under 35 U.S.C. 154(b) by 0 days.

(21) Appl. No.: 14/239,966

(22) PCT Filed: Aug. 24, 2012

(86) PCT No.: PCT/EP2012/066545
§ 371 (c)(1),
(2), (4) Date: May 7, 2014

(87) PCT Pub. No.: WO2013/030131
PCT Pub. Date: Mar. 7, 2013

(65) Prior Publication Data
US 2014/0309440 A1 Oct. 16, 2014

(30) Foreign Application Priority Data
Aug. 26, 2011 (FR) ...................................... 11 57563

(51) Int. Cl.
*C07D 307/48* (2006.01)
*C07D 307/50* (2006.01)

(52) U.S. Cl.
CPC ............ *C07D 307/48* (2013.01); *C07D 307/50* (2013.01)

(58) Field of Classification Search
CPC .................................................... C07D 307/48
USPC ........................................................ 549/489
See application file for complete search history.

(56) References Cited

U.S. PATENT DOCUMENTS 2,999,783 A 9/1961 Tomio et al.
7,572,925 B2 8/2009 Dumesic et al.

OTHER PUBLICATIONS

International Search Report for PCT/EP2012/066545 dated Nov. 5, 2012.
Sharma D K et al: "Elevated temperature hydrolysis of rice husk with pressurized water in a semibatch process", Cellulose Chemistry and Technology, Editura Academiei Romane, RO, vol. 17, No. 6, (Jan. 1, 1983), pp. 655-658.
Amar Singh et al: "Integrated process for production of xylose, furfural, and glucose from bagasse by two-step acid hydrolysis", Industrial & Engineering Chemistry Product Research and Development, vol. 23, No. 2, (Jun. 1, 1984), pp. 257-262.
Ajit Singh Mamman et al: "Furfural: Hemicellulose/xylosederived biochemical", Biofuels, Bioproducts and Biorefining, vol. 2, No. 5, (Sep. 1, 2008), pp. 438-454.
Xuejun Shi et al: "Selective Preparation of Furfural from Xylose over Sulfonic Acid Functionalized Mesoporous Sba-15 Materials", Energies, vol. 4, (2011), pp. 669-684.
Sergio Lima et al: "Catalytic cyclodehydration of xylose to furfural in the presence of zeolite H-Beta and a micro/mesoporous Beta/TUD-1 composite material", Applied Catalysis A:General, Elsevier B.V., vol. 388 (2010), pp. 141-148.
Ronen Weingarten et al: "Kinetics of furfural production by dehydration of xylose in a biphasic reactor with microwave heating", Green Chemistry, The Royal Society of Chemistry vol. 12, (Feb. 23, 2010), pp. 1423-1429.
Ronen Weingarten et al: "Design of solid acid catalysts for aqueous-phase dehydration of carbohydrates: The role of Lewis and Bronsted acid sites", Journal of Catalysis, Elsevier Inc., vol. 279 (2011), pp. 174-182.
Claude Moreau et al: "Selective preparation for furfural from xylose over microporous solid acid catalysts", Industrial Crops and Products, Elsevier B.V., vol. 7 (1998), pp. 95-99.

*Primary Examiner* — Taofiq A Solola
(74) *Attorney, Agent, or Firm* — B. Aaron Schulman, Esq.; Stites & Harbison, PLLC

(57) ABSTRACT

The invention relates to a method for preparing furfural by reacting pentose in water and in the presence of carboxylic acid and of a heterogeneous acid catalyst, the method being conducted in an aqueous solution of carboxylic acid as a reaction medium. The present invention also relates to the preparation of furfural by reaction of pentose in water and in the presence of carboxylic acid and of a heterogeneous acid catalyst. The invention also relates to an aqueous solution of carboxylic acid rich in furfural.

19 Claims, 3 Drawing Sheets

METHOD FOR PREPARING FURFURAL

The present invention relates to the preparation of furfural

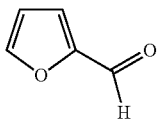

by dehydration of pentoses, of their derivatives, or of raw materials comprising pentoses or pentosans.

Furfural is a product stemming from the degradation of biomass. Furfural is notably used in the petrochemical field, for example for refining. Furfural, as well as its derivative furfuryl alcohol, may be used alone or associated with phenol, acetone, or urea for making furanic resins. Furfural is also used as a synthesis intermediate for producing solvents such as furanes and tetrahydrofurane.

Presently, furfural is essentially produced in China via batch processes called <<Quaker Oats>> processes. This process consists in dehydration of xylose in a sulfuric acid medium. However, this method consumes a lot of energy for a low furfural yield (30-35%).

The dehydrations conducted in an aqueous medium are not selective. The lack of selectivity of the reaction of dehydration of pentoses into furfural is explained by the rapidity of the secondary polymerization reactions of the reaction intermediates or of furfural in an aqueous medium (for example humin formation). Various methods have been developed for attempting to improve conversion into pentoses and furfural selectivity.

A method is known from WO2007/146636, which allows preparation of furfural from xylose in a biphasic medium comprising an acid aqueous phase formed with water, DMSO and HCl, as a catalyst, and an organic phase comprising MIBK and 2-butanol. The furfural produced in the aqueous phase is extracted by means of an organic solvent. This document describes in a more general way the dehydration of carbohydrates into furane derivatives, in a biphasic medium and preferentially in the presence of a mineral acid as a homogeneous catalyst.

The dehydration of xylose into furfural in a water/toluene mixture in the presence of H-Y faujasites and H-modenites is also known from Moreau et al. (Industrial Crops and Products, 1998, 7, 95-99). The dehydration of xylose into furfural in a water/toluene mixture in the presence of a zeolite is also known from Lima et al. (Applied Catalysis A: General 388, 2010, 141-148). Finally, the dehydration of xylose into furfural in a water/toluene mixture in the presence of mesoporous catalysts functionalized with sulfonic acid groups is known from Wang et al. (Energies, 2011, 670-684).

However, this type of method requires the use of solvents which may be toxic, therefore requiring purifications of the obtained furfural, and for which the boiling temperatures are high, which are makes these methods, complex and costly.

The use of a solid acid catalyst for dehydration of xylose into furfural in water is known from Hubert et al. (Journal of Catalysis, 2011, 279, 174-182). The dehydration of xylose into furfural in an aqueous solution containing HCl or in a biphasic water/organic solvent medium by heating with microwaves is also known from Hubert et al. (Green Chemistry, 2010, 12, 1423-1429).

Thus, in order to increase the conversion into pentoses and the furfural selectivity, increasingly complex techniques have been developed, without however reaching the expected yields.

Production of furfural in a selective way is complex and its purification is difficult because of the instability of this molecule.

Therefore, there is an advantage in providing a method for preparing furfural which meets the drawbacks of the methods of the state of the art.

An object of the present invention is to provide a method for preparing furfural which is advantageous from an industrial point of view.

Another object of the present invention is to provide a method for preparing furfural with high selectivity and conversion.

Still another object of the present invention is to provide a method for preparing furfural giving the possibility of reducing, or even suppressing, the formation of secondary byproducts notably of the humin type.

An object of the invention is also to provide a method which may be conducted in an aqueous medium and without requiring potentially toxic organic solvents, with or without catalysts. Other objects will become apparent upon reading the following description of the invention.

All these objects are fulfilled by the invention which relates to a method for preparing furfural by reaction of pentoses in water and in the presence of a carboxylic acid. Advantageously, the method is conducted in an aqueous solution of a carboxylic acid as a reaction medium, either in the presence or not of a heterogeneous catalyst. Advantageously, with the method of the invention, it is possible to obtain conversions into pentose, notably xylose, of more than 50%, preferably more than 90%. Advantageously, with the method of the invention, it is possible to obtain furfural selectivity of more than 50%, preferably more than 75%.

According to the invention, by <<pentoses>>, are meant, in addition to cyclic compounds of chemical formula $C_5H_{10}O_5$ such as xylose or arabinose or mixtures thereof, pentose derivatives and products comprising pentoses or their derivatives.

By <<pentose derivatives>>, are meant compounds comprising in their structure at least one pentose unit, which may notably be obtained by depolymerization of raw materials rich in pentosans. The pentose derivatives according to the invention are notably polymers of xylose, notably xylan, and hemicelluloses of various origins.

According to the invention, the <<products comprising pentoses or their derivatives>> may be represented by lignocellulose biomass stemming from softwood or hardwood lumber, a biomass which corresponds to an assembly of cellulose, hemicellulose and lignin; stemming from annual plants, such as sugar cane, cereals, beets, etc.; stemming from coproducts of the agri-feed industry such as straw, sugar cane bagasse, pentose-rich sweet juices stemming from pretreatments of biomass. Hemicelluloses and lignocellulose biomass may be used as such in the method of the invention. They may also be pretreated, for example with mechanical and/or steam explosion treatments or with ammonia and/or with chemical treatments, notably by more or less intensive hydrolysis, in order to have a raw material which is rich in more or less depolymerized pentosans, before being subject to conversion in the aqueous carboxylic acid medium of the invention.

The pentose is notably selected from xylose, arabinose, derivatives of pentoses such as the hemicellulose fraction of biomass, liquid hemicellulose extracts rich in more or less depolymerized pentosans stemming from agricultural or forest coproducts.

Preferably, the pentose is xylose and/or arabinose. Preferably the pentose is xylose.

The carboxylic acids may be mono-acids, diacids or triacids. They are notably selected from:
- acids of formula R—COOH wherein R represents a hydrogen atom or a linear or branched $C_1$-$C_5$, preferably $C_1$-$C_3$, alkyl chain, optionally substituted with one or several OH groups;
- acids of formula HOOC-L-COOH wherein L represents a bond or a linear or branched $C_1$-$C_5$, preferably $C_1$-$C_3$ alkyl chain, optionally substituted with one or several OH and/or COOH groups; and
- mixtures thereof.

Preferably, the acid is a mono-acid, notably of formula R—COOH wherein R represents a hydrogen atom or a linear or branched $C_1$-$C_5$, preferably $C_1$-$C_3$, alkyl chain, optionally substituted with one or several OH groups.

Preferably, the carboxylic acid is formic acid, acetic acid, malic acid, citric acid, oxalic acid, lactic acid or mixtures thereof.

More preferably, the carboxylic acid is acetic acid. This acid has the advantage of being stable in the reaction medium and of being easily removed notably by evaporation in vacuo. Advantageously, when the carboxylic acid is acetic acid, the conversion of the initial pentose, for example xylose, and the purification of the obtained furfural is facilitated because of the volatility of acetic acid. It will thus be possible to obtain a furfural-rich acetic acid composition which may be directly used, notably for preparing a polymer, for example of furane resins; or to purify this solution so as to obtain pure furfural.

The presence of the acid according to the invention, as compared with the same method exclusively applied in the presence of water, gives the possibility of significantly increasing the conversion of pentoses, for example xylose, the furfural yield and selectivity. One skilled in the art, depending on whether he/she prefers to promote conversion of pentose, for example xylose, or furfural selectivity or to have a good compromise between both of these characteristics, may determine the proportion and the nature of the acid to be integrated to the reaction medium.

The inventors have shown that by controlling the acid concentration, it is possible, in a particularly advantageous and surprising way, to obtain significant HMF yield and selectivity.

At a low acid concentration, the HMF yield is very low or even zero and at a high acid concentration, the HMF yield is low and levullinic acid is obtained as a byproduct in substantial amounts.

The amount of acid should however not be too large with the risk of increasing the production of byproducts, notably humin. Thus, preferably the amount of acid is less than 80% by weight, generally comprised between 5 and 80% by weight, notably comprised between 5 and 70% by weight, more preferentially between 10 and 50% by weight, for example 20% or 10% by weight based on the total weight of water+carboxylic acid.

Further, it has been shown by the inventors that surprisingly, the carboxylic acids, and in particular acetic acid, gave the possibility of stabilizing the furfural formed in the aqueous medium.

In the method according to the invention, water is preferably present in an amount greater than or equal to 20% by weight, generally in an amount comprised between 20 and 95% by weight, preferably between 30 and 95% by weight, for example between 50 and 90% by weight, for example from 80 to 90% by weight based on the total weight of water+carboxylic acid.

In the method of the invention, the amount of pentose, for example xylose, depends on its solubility limit in the mixture of water and carboxylic acid. It is generally comprised between 0.5 and 10%, preferably between 1% and 10%, more preferentially between the 0.5 and 5%, notably between 0.8 and 2%, for example about 1%, based on the total weight of water+carboxylic acid.

The method according to the invention may be conducted at a temperature comprised between 100 and 200° C., preferably between 120 and 180° C., for example between 150 and 180° C.

The method according to the invention may be applied at atmospheric pressure or under pressure of an inert gas, for example helium, up to a pressure of about 3.5 MPa (i.e. about 35 bars).

The method of the invention may advantageously be applied in the presence of a heterogeneous acid catalyst. Surprisingly, the inventors have shown that the association of a carboxylic acid with a heterogeneous acid catalyst produces a synergistic effect on the conversion of pentoses and on the furfural yield. The synergy may be evaluated by Colby's method by using the formula $E=X+Y-(XY/100)$ wherein:

E represents the expected furfural yield by applying the acid and the catalyst simultaneously, X represents the obtained furfural yield by applying the acid alone, Y represents the obtained furfural yield by applying the catalyst alone.

When the experimental furfural yield is greater than E, the synergistic effect is demonstrated. Preferably, the catalyst is selected from polyoxometallates (heteropolyacids) like 12-tungstophosphoric acid, preferably dispersed on niobium oxide, zirconium oxide, titanium dioxide, alumina, sulfated zirconias; tungstated zirconias (ZrW), cesium acid salts of 12-tungstophosphoric acid ($Cs_2HPW_{12}O_{40}$); coals and derivatives, for example sulfonated coals, functionalized coals, for example with carboxylic groups, for example subsequently to oxidation, for example oxidation with sodium hypochlorite, coals impregnated with a nafion solution, active coals, mesoporous coals, exfoliated graphites, or their mixtures, zeolites like USY, Beta, MCM-22, ZSM-5, clays like montmorillonite, optionally having been exchanged with transition metals, protonic clays notably of the K10 type, phosphates like niobium or Fe phosphates, resins like Amberlyst® 15 or Nafion®, niobium oxide or their mixtures.

Preferably, the catalyst is selected from polyoxometallates (heteropolyacids) like 12-tungstophosphoric acid, preferably dispersed on niobium oxide, zirconium oxide, titanium dioxide, alumina, sulfated zirconias; tungstated zirconias (ZrW), cesium acid salts of 12-tungstophosphoric acid ($Cs_2HPW_{12}O_{40}$); coals and derivatives, for example sulfonated coals, functionalized coals, for example with carboxylic groups, for example subsequent to oxidation, for example oxidation with sodium hypochlorite, coals impregnated with a nafion solution, active coals, mesoporous coals, exfoliated graphites, or their mixtures, zeolites like USY, Beta, MCM-22, ZSM-5, clays like montmorillonite, optionally having been exchanged with transition metals, phosphates like niobium or Fe phosphates, resins like Amberlyst® 15 or Nafion®.

Notably, the addition of these catalysts advantageously gives the possibility of increasing the conversion of pentoses, for example xylose, and the furfural yield. Furfural selectivity is improved by the use of a heterogeneous catalyst.

More preferably, the catalyst is a sulfonated coal, a coal functionalized with carboxylic functions or a coal impregnated with solutions of carboxylic acids or other acids or a coal treated with oxidizers (sodium hypochlorite, hydrogen peroxides) in order to increase its surface acidity.

More preferably, the catalyst is a sulfonated coal.

When it is present, the amount of catalyst is preferably comprised between 2 and 100% by weight, preferably between 2 and 10% by weight, for example about 5% by weight based on the weight of pentoses, for example xylose.

The presence of a heterogeneous catalyst advantageously allows improvement in the furfural selectivity while reducing the reaction temperature.

Preferably, the method is applied in the presence of a catalyst and at a temperature comprised between 100 and 150° C., for example at about 150° C.

It is thus possible to obtain conversion ranging up to 80% of the pentoses with a selectivity which may range up to 95%.

The method according to the invention may be applied batchwise or continuously. Advantageously, it will be applied continuously. If a heterogeneous acid catalyst is used, the method will advantageously be applied continuously, preferably on a fixed bed of catalyst.

The invention also relates to aqueous solutions of carboxylic acid comprising furfural, preferably comprising from 0.1 to 10% by weight of furfural, for example from 0.3 to 6% by weight of furfural and which may comprise from 0 to 5% by weight of pentose, for example xylose, for example from 0 to 0.5% by weight of pentose, for example xylose. These solutions may be obtained by the method of the invention and therewith.

More particularly, the invention relates to an aqueous solution of acetic acid comprising furfural, preferably comprising from 0.1 to 10% by weight of furfural and which may comprise from 0 to 5% by weight of pentose, for example xylose. Preferably, this solution does not comprise any pentose, for example any xylose, and may be directly used, notably for preparing polymers and resins, notably furane resins.

Captions in the figures: yld=yield, AcAc=acetic acid, Ac=acid, (cata=heterogeneous catalyst).

The present invention will now be described by means of non-limiting examples.

EXAMPLE 1

Influence of Temperature on the Production of Furfural in a Water/Acetic Acid Medium Synthesis of furfural is achieved in a 100 ml autoclave. The following amounts are introduced into the reactor: 48 g of distilled water to which are added 12 g of acetic acid and 0.6 g of xylose (1%). The reaction is conducted under a helium atmosphere (20 bars). The reaction medium is stirred by means of a magnetic stirrer. The reaction medium is brought to the reaction temperature by means of regulated electric resistors. The following temperatures are studied: 120° C., 150° C., 180° C. After 15 hours of reaction, the reaction medium is cooled by means of an ice bath. The conversion of xylose and the furfural yield are determined by HPLC-RID analysis (column: COREGEL 87C).

Figure 1:
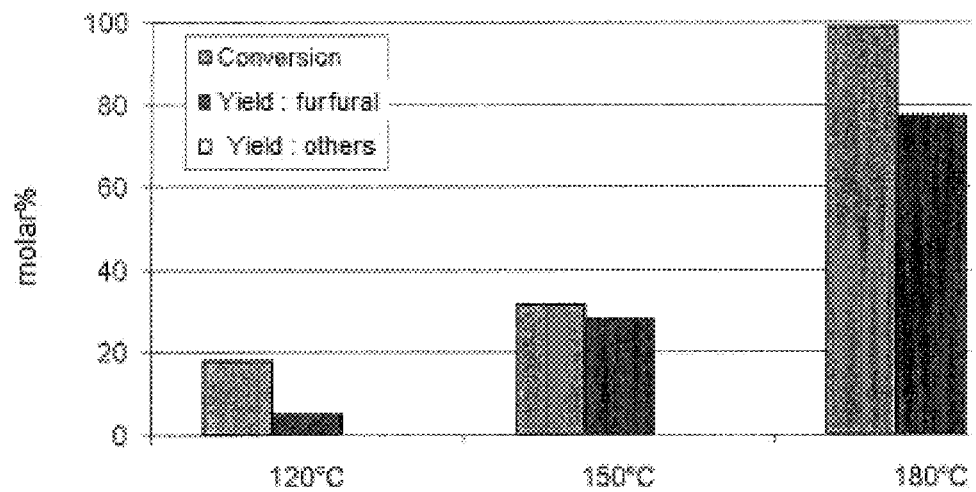
FIG. 1 illustrates the influence of temperature on the conversion of xylose into furfural.

The results are shown in FIG. 1. The results show that the conversion of xylose and the furfural yield are low at 120° C. FIG. 1 shows an increase in the conversion of xylose and in the furfural yield with increase in temperature. The best compromise between the conversion of xylose and the furfural yield is obtained at the temperature of 150° C.; a furfural selectivity of 89% is obtained. It is also observed that at the temperature of 180° C., the conversion of xylose is complete and the furfural molar yield is close to 80%.

EXAMPLE 2

Influence of the Carboxylic Acid Content

The synthesis of furfural is achieved in a 100 ml autoclave. The following amounts are introduced into the reactor: 0.6 g of xylose (1%), 60 g of an aqueous solution which may contain 10%, 20%, 50% by weight of acetic acid or 60 g of acetic acid. The reaction is applied under a helium atmosphere (20 bars). The reaction medium is stirred by means of a magnetic stirrer. The reaction medium is brought to the reaction temperature by means of electric resistors regulated to 180° C. After 15 hours of reaction at 180° C., the reaction mixture is cooled by means of an ice bath. The conversion of xylose and the furfural yield are determined by HPLC-RID analysis (column: COREGEL 87C).

The method was applied with acetic acid in different proportions, 10%, 20%, 50% by weight of the aqueous reaction medium comprising xylose. The method was also applied with a reaction medium only comprising acetic acid and xylose.

Figure 2:
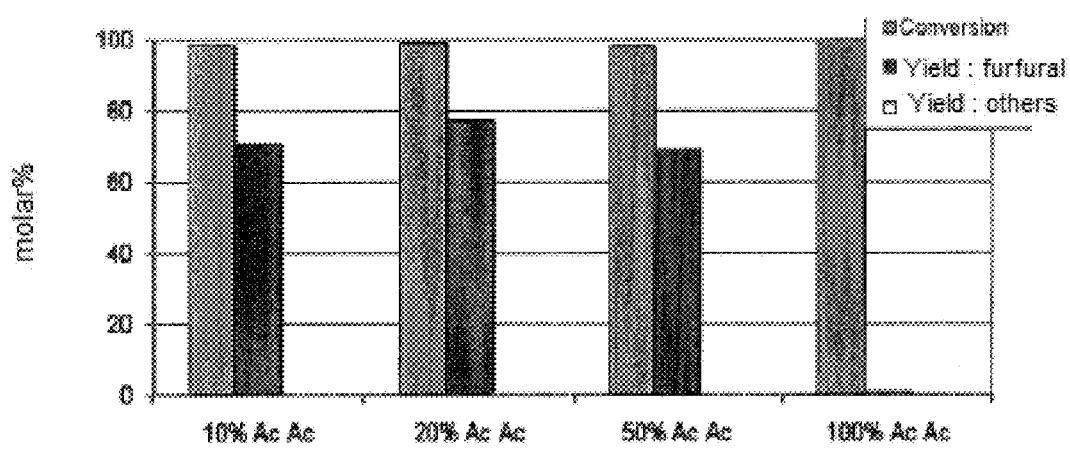
FIG. 2 illustrates the influence of the acetic acid concentration on the conversion of xylose into furfural at 180° C.

The obtained results are shown in FIG. 2. The results show that for large amounts of carboxylic acid, conversion of xylose increases, but the furfural selectivity decreases. Thus, when the reaction is applied with 100% of acetic acid, a very small amount of furfural is obtained.

The best compromise between conversion of xylose and furfural selectivity is obtained with an aqueous solution comprising 20% of acetic acid.

EXAMPLE 3

Influence of the Nature of the Carboxylic Acid

The synthesis of furfural is achieved in a 100 ml autoclave. The following amounts are introduced into the reactor: 60 g of an aqueous solution containing 20% by weight of carboxylic acid, 0.6 g of xylose.

The aqueous solutions of carboxylic acid have the following compositions:
12 g of lactic acid to 48 g of distilled water; or
12 g of acetic acid added to 48 g of distilled water; or
12 g of formic acid added to 48 g of distilled water.

The reactions are conducted under a helium atmosphere (20 bars). The reaction medium is stirred by means of a magnetic stirrer. The reaction medium is brought to the reaction temperature by means of electric resistors regulated to 180° C. After 15 hours of reaction at 180° C., the reaction mixture is cooled by means of an ice bath. The conversion of xylose and the furfural yield are determined by HPLC-RID analysis (column: COREGEL 87C)

Figure 3:
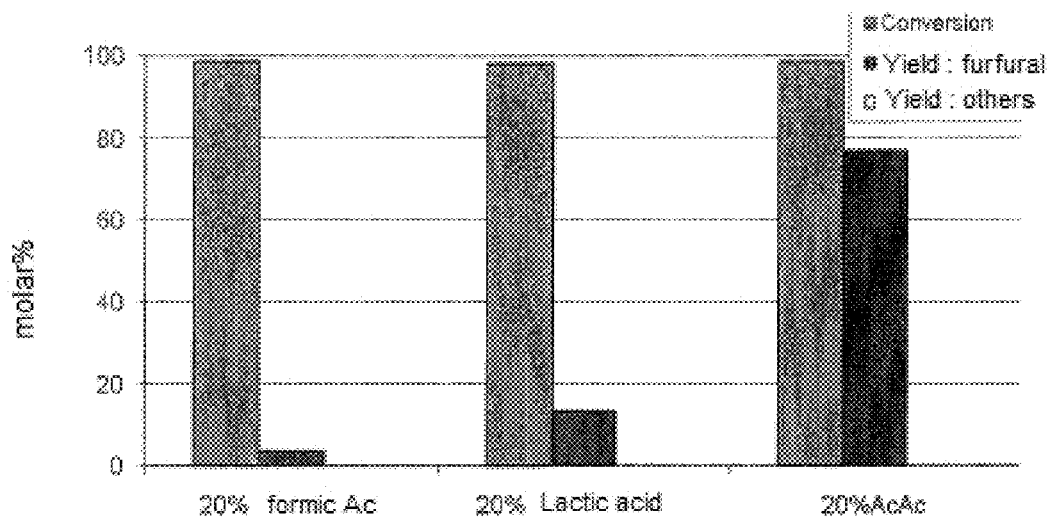
FIG. 3 illustrates the influence of the nature of the carboxylic acid on the conversion of the pentose into furfural at 180° C.

The obtained results are shown in FIG. 3. The results show that the conversion of xylose is complete but that the furfural yield is low in the presence of formic acid and lactic acid. The best compromise between conversion and furfural yield is obtained with acetic acid.

EXAMPLE 4

Influence of the Xylose Content in the Initial Reaction Medium

The synthesis of furfural is achieved in a 100 ml autoclave. The following amounts are introduced into the reactor: 48 g of distilled water and 12 g of acetic acid to which are added 0.3 g of xylose (0.5%), or 0.6 g of xylose (1%), or 3 g of xylose (5%) or 6 g of xylose (10%). The reactions are applied under a helium atmosphere (20 bars). The reaction medium is stirred by means of a magnetic stirrer. The reaction medium is brought to the reaction temperature by means of electric resistors regulated to 180° C. After 15 hours of reaction at 180° C., the reaction mixture is cooled by means of an ice bath. The conversion of xylose and the furfural yield are determined by HPLC-RID analysis (column: COREGEL 87C)

Figure 4:
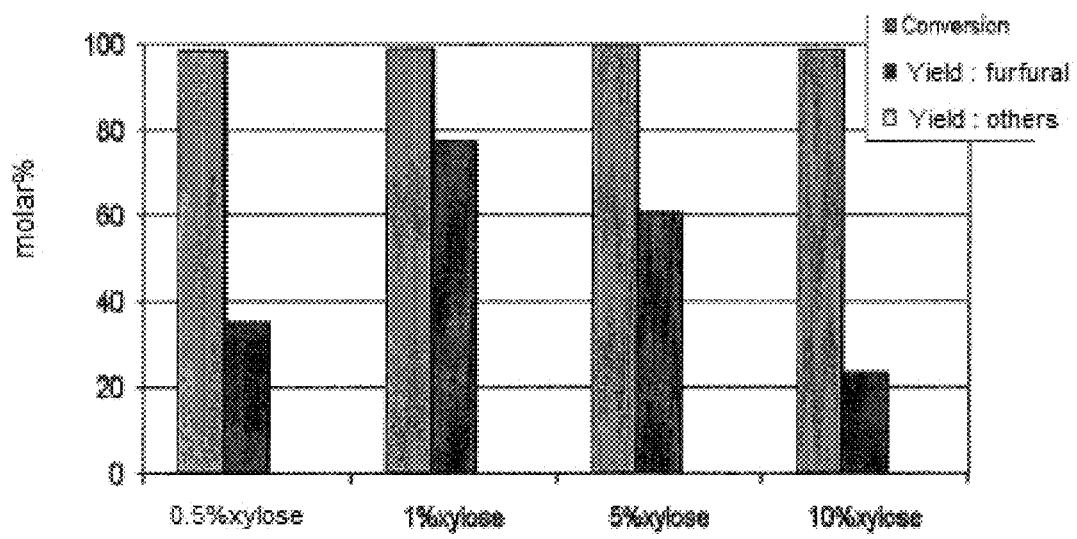
FIG. 4 illustrates the influence of the xylose concentration on the conversion at 180° C.

The results are shown in FIG. 4. The results show that the conversion of xylose and the furfural yield depend on the xylose concentration. The results show that the best furfural yield is obtained for 1% of xylose.

EXAMPLE 5

Influence of the Addition of Heterogeneous Acid Catalysts

The synthesis of furfural is achieved in a 100 ml autoclave. The following amounts are introduced into the reactor: 48 g of distilled water, 12 g of acetic acid, 0.6 g of xylose, 30 mg of catalyst. The catalyst is used without any pretreatment. The reactions are conducted under a helium atmosphere (20 bars). The reaction medium is stirred by means of a magnetic stirrer. The reaction medium is brought to the reaction temperature by means of electric resistors regulated to 150° C. After 15 hours of reaction at 150° C., the reaction mixture is cooled by means of an ice bath. The catalyst is separated by filtration. The conversion of xylose and the furfural molar yield are determined by HPLC-RID analysis (column: COREGEL 87C)

The method was applied in the absence of any heterogeneous catalyst and in the presence of various catalysts, i.e. sulfonated coal (sulfonated C), coal impregnated with a nafion solution, sulphated zirconias (ZrW), a cesium acid salt of 12-tungstophosphoric acid ($Cs_2H$: $Cs_2HPW_{12}O_{40}$). The method was also applied in the absence of acetic acid (in a purely aqueous medium) and in the presence of sulfonated coal.

Figure 5:
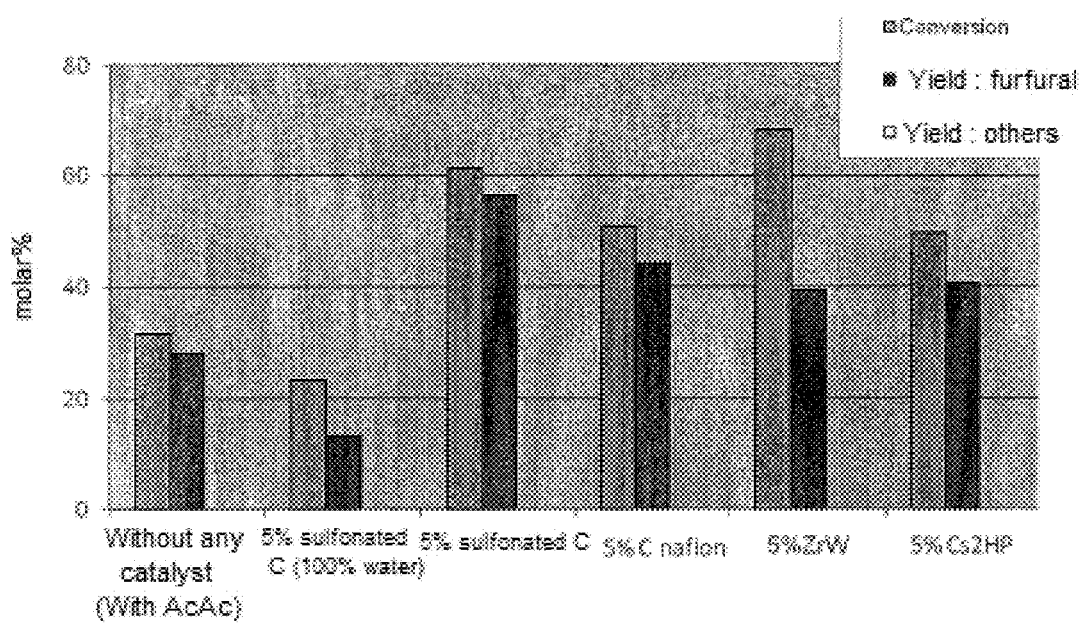
FIG. 5 illustrates the influence of the presence of a heterogeneous catalyst on the conversion of xylose into furfural at 150° C.

The obtained results are shown in FIG. 5. The results show that by adding a catalyst, it is possible to increase the conversion of xylose. The results notably show that the best comprise between the conversion of xylose and furfural yield is obtained with the sulfonated coal used in the aqueous solution containing 20% by weight of acetic acid, the furfural selectivity is then close to 95% for a conversion of xylose of more than 60%.

EXAMPLE 6

Influence of the Catalyst Content

The synthesis of furfural is achieved in a 100 ml autoclave. The following amounts are introduced into the reactor: 48 g of distilled water, 12 g of acetic acid, 0.6 g of xylose and in the absence or in the presence of a heterogeneous catalyst. The reactions are conducted under a helium atmosphere (20 bars). The reaction medium is stirred by means of a magnetic stirrer. The reaction medium is brought to the reaction temperature by means of electric resistors regulated to 150° C. After 15 hours of reaction at 150° C., the reaction mixture is cooled by means of an ice bath. The catalyst is separated by filtration. The conversion of xylose and the furfural molar yield are determined by HPLC-RID analysis (column: COREGEL 87C)

The method was applied in the absence of any catalyst and in the presence of 30 mg, 60 mg or 90 mg of sulfonated coal.

Figure 6:
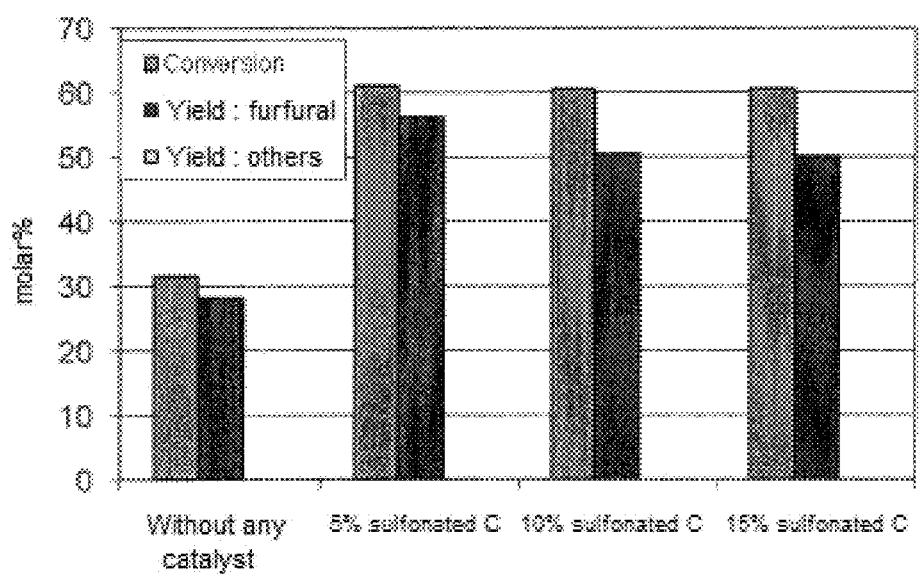
FIG. 6 illustrates the influence of the heterogeneous catalyst content on the conversion of xylose into furfural at 150° C.

The obtained results are shown in FIG. 6. The results show that the catalyst content has little influence on the conversion and yield. The best results are obtained for a reaction medium comprising 5% of catalyst based on the weight of xylose.

EXAMPLE 7

Demonstration of the Synergy

The synthesis of furfural is achieved in a 100 ml autoclave. The following amounts are introduced into the reactor: 48 g of distilled water, 12 g of acetic acid, 0.6 g of xylose, 30 g of catalyst. The catalyst (K10, ZSM5 and sulfonated C) is used without any pretreatment. The reactions are conducted under a helium atmosphere (20 bars). The reaction medium is stirred by means of a magnetic stirrer. The reaction medium is brought to the reaction temperature by means of electric resistors regulated to 150° C. After 15 hours of reaction at 150° C., the reaction mixture is cooled by means of an ice bath. The catalyst is separated by filtration. The conversion of xylose and the furfural molar yield are determined by HPLC-RID analysis (column: COREGEL 87C).

As a comparison, the method was also applied in the absence of any catalyst but with 12 g of acetic acid and in the absence of acetic acid and with 30 mg of catalyst.

The results are given in Table 1. The result in terms of furfural yield was calculated by Colby's method and is noted (as E) in Table 1.

TABLE 1

| Tests | Conditions | Conversion | Furfural yield | E |
|---|---|---|---|---|
| 1 | Acetic acid alone | 32 | 28 | |
| 2 | K10 alone | 22 | 12 | |
| 3 | ZSM5 alone | 22 | 13 | |
| 4 | K10 + acetic acid | 62 | 40 | 36.64 |
| 5 | ZSM5 + acetic acid | 100 | 45 | 37.36 |
| 6 | 5% of sulfonated C alone | 23 | 13 | |
| 7 | 5% of sulfonated C + acetic acid | 61 | 56 | 37.36 |

The results show that the carboxylic acid and catalyst association is synergistic since the obtained furfural yield is greater than the expected yield according to Colby's method.

The invention claimed is:

1. A method for preparing furfural comprising reacting pentose in water and in the presence of carboxylic acid selected from the group consisting of:

the acids of formula R—COOH wherein R represents a hydrogen atom or a linear or branched $C_1$-$C_5$ alkyl chain, optionally substituted with one or several OH groups;

acids of formula HOOC-L-COOH wherein L represents a bond or a linear or branched $C_1$-$C_5$ alkyl chain, optionally substituted with one or several OH and/or COOH groups; and mixtures thereof, and a heterogeneous acid catalyst, the method being conducted in an aqueous solution of carboxylic acid as a reaction medium.

2. The method according to claim 1, for which the pentose is xylose, arabinose, derivatives of pentoses being the hemicellulose fraction of the biomass, hemicellulose liquid extracts rich in more or less depolymerized pentosans stemming from agricultural or forest coproducts.

3. The method according to claim 1, for which the pentose is xylose.

4. The method according to claim 1, for which the acid is selected from the group consisting of:

the acids of formula R—COOH wherein R represents a hydrogen atom or a linear or branched $C_1$-$C_3$ alkyl chain, optionally substituted with one or several OH groups;

acids of formula HOOC-L-COOH wherein L represents a bond or a linear or branched $C_1$-$C_3$, alkyl chain, optionally substituted with one or several OH and/or COOH groups; and mixtures thereof.

5. The method according to claim 1, for which the acid is acetic acid.

6. The method according to claim 1, for which the catalyst is selected from the group consisting of polyoxometallates (heteropolyacids) selected from the group consisting of 12-tungstophosphoric acid, tungstated zirconias (ZrW), and cesium acid salts of 12-tungstophosphoric acid ($Cs_2HPW_{12}O_{40}$); coals and derivatives selected from the group consisting of sulfonated coals, functionalized coals, impregnated coals, active coals, mesoporous coals, exfoliated graphites, and their mixtures; zeolites selected from the group consisting of USY, Beta, MCM-22 and ZSM-5; montmorillonite clays, optionally having been exchanged with transition metals, protonic clays, phosphates selected from the group consisting of niobium and Fe phosphates; resins selected from the consisting of Amberlyst® 15 and Nafion®; niobic acid; and their mixtures.

7. The method according to claim 1, for which the carboxylic acid is present in an amount from 5 to 70% by weight, based on the total water+carboxylic acid weight.

8. The method according to claim 1, for which the water is present in an amount greater than or equal to 20% by weight, based on the total water+carboxylic acid weight.

9. The method according to claim 1, carried out in the presence of a heterogeneous acid catalyst, a method for which the amount of catalyst is comprised between 1 and 100% by weight based on the weight of pentose.

10. The method according to claim 1, for which the amount of pentose is comprised between 0.5 and 10%, by weight based on the total water+carboxylic acid weight.

11. The method according to claim 1, conducted at a temperature ranging from 100 to 200° C.

12. The method according to claim 1, wherein the method is conducted continuously.

13. An aqueous solution of carboxylic acid comprising furfural which may be obtained according to the method of claim 1, comprising from 0.1 to 10% by weight of furfural and 5 to 70% of carboxylic acid by weight based on the total water+acid carboxylic weight.

14. An aqueous solution according to claim 13 comprising 10 to 50% of carboxylic acid by weight based on the total water+acid carboxylic weight.

15. The method according to claim 1, wherein the water is present in an amount ranging from 30 to 95% by weight based on the total water+carboxylic acid weight.

16. The method according to claim 1, wherein the carboxylic acid is present in an amount from 10 to 50% by weight based on the total water+carboxylic acid weight.

17. The method according to claim 1, wherein the carboxylic acid is present in an amount of 20% by weight based on the total water+carboxylic acid weight.

18. The method according to claim 1, wherein the method is carried out in the presence of a heterogeneous acid catalyst, and wherein the amount of catalyst comprises between 2 and 10% by weight based on the weight of pentose.

19. The method according to claim 6, wherein 12-tungstophosphoric acid is dispersed on niobium oxide, zirconium oxide, titanium dioxide, alumina, and sulfated zirconias; wherein coals are functionalized with carboxylic groups; said coals being impregnated with a Nafion® solution; and wherein protonic clays are of the K10 type.

\* \* \* \* \*